(12) United States Patent
Chandra

(10) Patent No.: US 9,924,977 B2
(45) Date of Patent: Mar. 27, 2018

(54) TECHNIQUES FOR REDUCTION OF BASILAR INVAGINATION AND ATLANTO AXIAL DISLOCATION AND SURGICAL INSTRUMENTS THEREOF

(71) Applicant: All India Institute of Medical Sciences, New Delhi (IN)

(72) Inventor: Sarat P. Chandra, New Delhi (IN)

(73) Assignee: All India Institute of Medical Sciences, New Delhi (IN)

( * ) Notice: Subject to any disclaimer, the term of this patent is extended or adjusted under 35 U.S.C. 154(b) by 108 days.

(21) Appl. No.: 14/897,156

(22) PCT Filed: Jun. 9, 2014

(86) PCT No.: PCT/IN2014/000385
§ 371 (c)(1),
(2) Date: Dec. 9, 2015

(87) PCT Pub. No.: WO2014/199398
PCT Pub. Date: Dec. 18, 2014

(65) Prior Publication Data
US 2016/0128736 A1    May 12, 2016

(30) Foreign Application Priority Data

Jun. 10, 2013 (IN) .......................... 1724/DEL/2013
Jun. 6, 2014 (IN) .......................... 1521/DEL/2014

(51) Int. Cl.
*A61B 17/88* (2006.01)
*A61B 17/70* (2006.01)
*A61B 17/02* (2006.01)

(52) U.S. Cl.
CPC ...... *A61B 17/7055* (2013.01); *A61B 17/7053* (2013.01); *A61B 17/025* (2013.01); *A61B 17/7035* (2013.01); *A61B 2017/0256* (2013.01)

(58) Field of Classification Search
CPC ............ A61B 17/7055; A61B 17/7053; A61B 17/025; A61B 17/7035; A61B 2017/0256
(Continued)

(56) References Cited

U.S. PATENT DOCUMENTS

2008/0097433 A1    4/2008  Molz
2008/0234755 A1*   9/2008  Henderson ......... A61B 17/7055
                                                    606/298

(Continued)

OTHER PUBLICATIONS

Chandra, P. Sarat et al., "Distraction, Compression, and Extension Reduction of Basilar Invagination and Atlantoaxial Dislocation: A Novel Pilot Technique" Neurosurgery, Jun. 2013, pp. 1040-1053, vol. 72, No. 6.

(Continued)

*Primary Examiner* — Pedro Philogene
*Assistant Examiner* — David C Comstock
(74) *Attorney, Agent, or Firm* — Knobbe Martens Olson & Bear LLP

(57) ABSTRACT

The present invention pertains to the field of neurosurgery and describes new methods to reduce basilar invagination (BI) and atlanto-axial dislocation (AAD). The invention further discloses novel surgical instruments useful in reducing basilar invagination (BI) and atlanto-axial dislocation (AAD). The novel techniques disclosed include distraction, compression and extension reduction and dynamic distraction coupled with cable compression.

25 Claims, 13 Drawing Sheets

(58) Field of Classification Search
USPC .................................................. 606/263, 279
See application file for complete search history.

(56) References Cited

U.S. PATENT DOCUMENTS

| | | |
|---|---|---|
| 2009/0018584 A1 | 1/2009 | Henderson, Sr. et al. |
| 2009/0105820 A1* | 4/2009 | Jackson ............. A61B 17/7004 623/17.11 |
| 2012/0215260 A1 | 8/2012 | Paul et al. |

OTHER PUBLICATIONS

Jian, Feng-Zeng et al., "Direct Posterior Reduction and Fixation for the Treatment of Basilar Invagination With Atlantoaxial Dislocation" Neurosurgery, Apr. 2010, pp. 678-687, vol. 66, No. 4.
International Search Report for PCT/IN14/00385 dated Mar. 11, 2015.

* cited by examiner

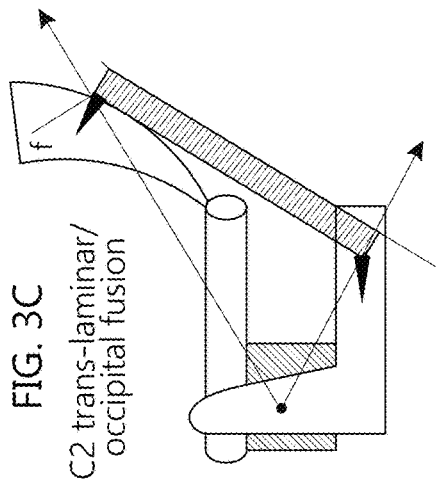

FIG. 3A
Goel & Harms

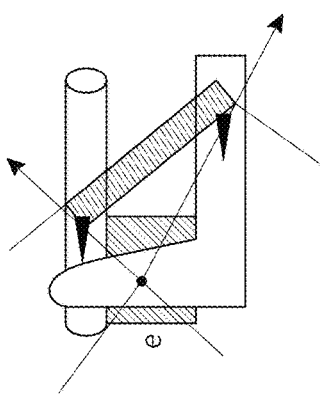

FIG. 3B
C2 trans-laminar/ C1 lateral mass fusion

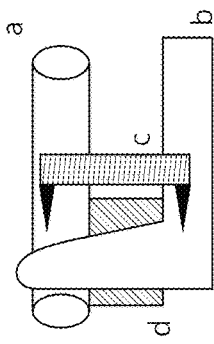

FIG. 3C
C2 trans-laminar/ occipital fusion

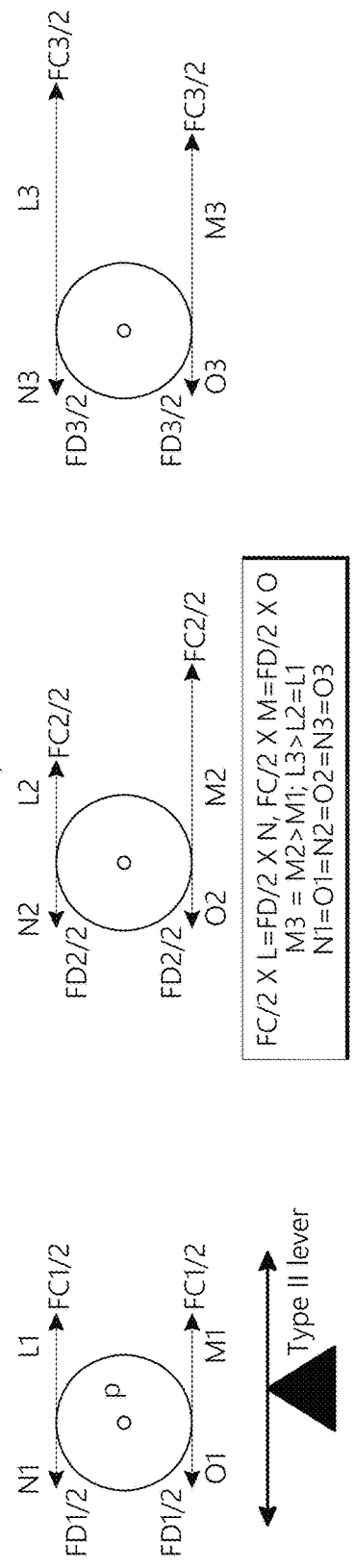

FIG. 3 a=C1 arch, b=C2 arch, c=implant, d=inter facet spacer, e=the center point of the spacer, f=occiput, p=pivot/fulcrum, FC=the compressive force generated by the implant and is the function of the levers L and M, which are variable depending on the technique. FD=the distractive force generated by the spacer and is a function of the length of the lever arms N and O, which are constant in all the 3 techniques. Both FC and FD become equally divided over the superior and inferior aspects of the implant, hence the values FD/2 & FC/2. FC should be > FD to maintain the stability of the construct and to keep the cranio-vertebral junction in reduced and well aligned position. Type II lever: pivot or fulcrum in center and lever arms on either side.

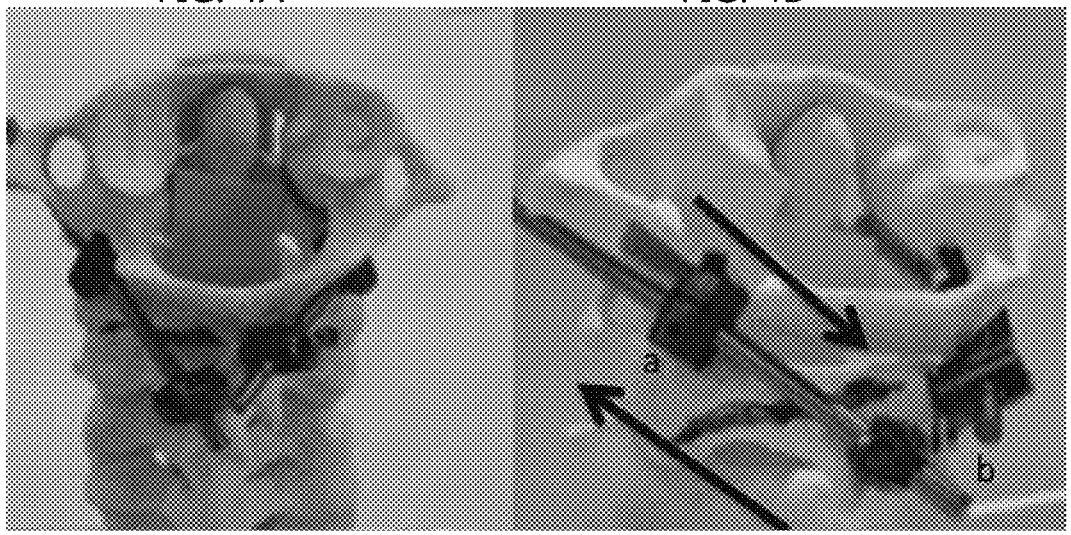
FIG. 4A   FIG. 4B
FIG. 4C   FIG. 4D
FIG. 4

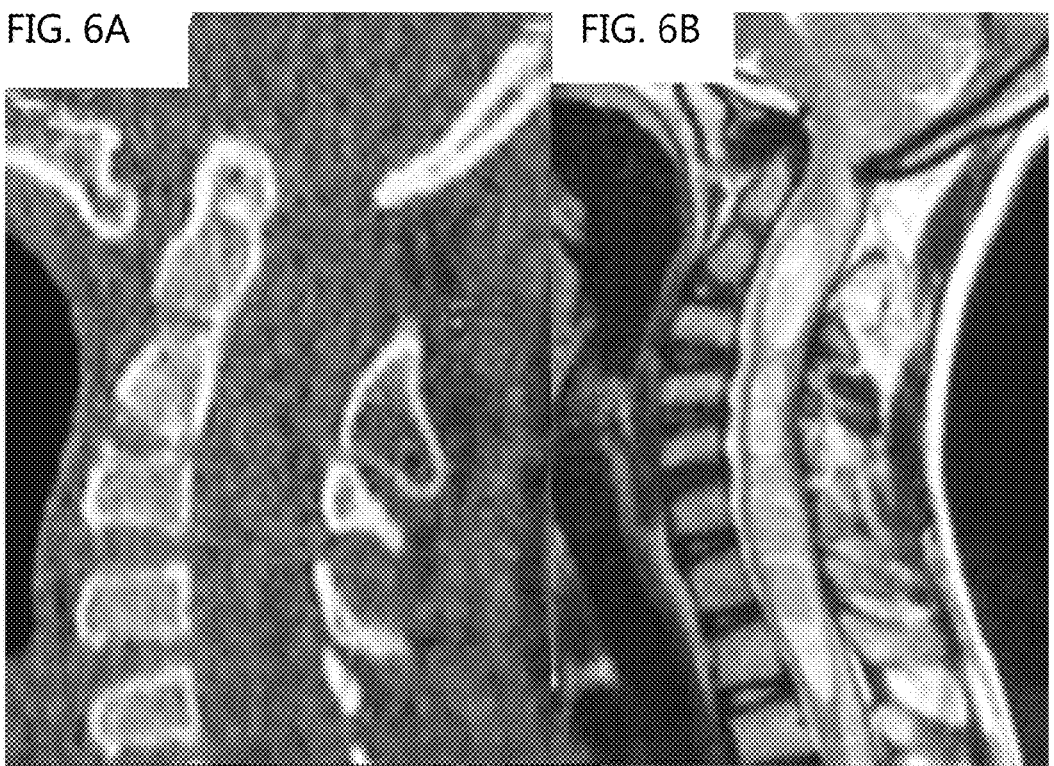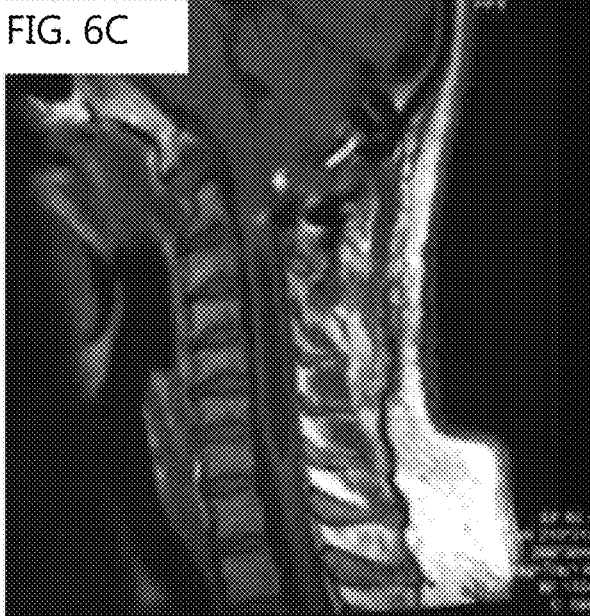
FIG. 6

Graphical depiction of the various radiological measurements pre and post op.
CL=Chamberlein's line; CCA=Clivus canal angle; ML=Mc Rae's line; RL=Modified Ranawt's line; WL=Wackenheim line. The graphs on the left correspond to pre op values and those on right side correspond to post op values; negative values indicate distance of dens above this line CL; normal range=dens is about 2.3 ± 2.6 mm below this line. Mean pre op value = 11 ± 6.7mm; mean post op=2.3 ± 1.9 mm below the line CCA; normal range=> 150 deg. Mean pre op angle=116 + 19 deg; mean post op angle=149 + 8 deg ML; normal range=dens 5.8 ± 1.6 mm below this line. Mean pre-op=10.8 + 5.8 mm above the line; mean post op=2.8 + 1.7 mm RL; Normal value= 29.7 ± 2.6mm. Mean pre op distance=8.7 ± 6.9mm; mean post op distance= 24 ± 18mm WL; normal range= dens 0.9 ± 2.2mm below this line. mean pre op value 8.2 + 3.4mm; mean post op value of 1.2 + 0.6mm below the line

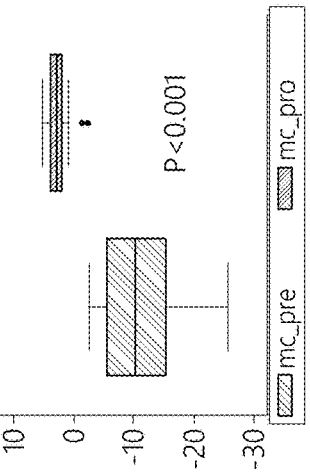
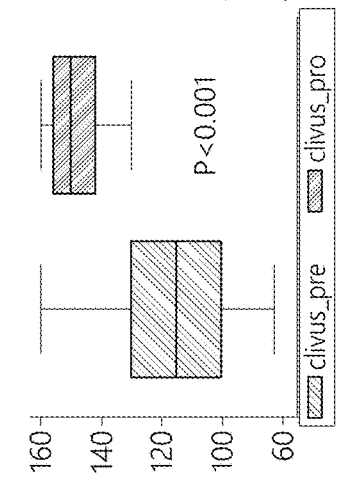
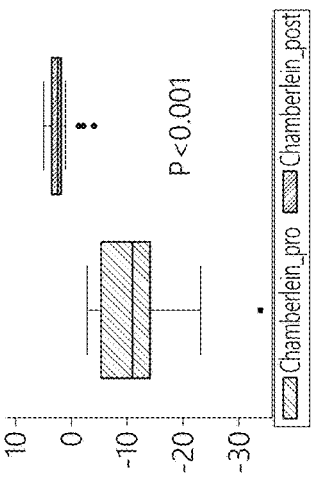
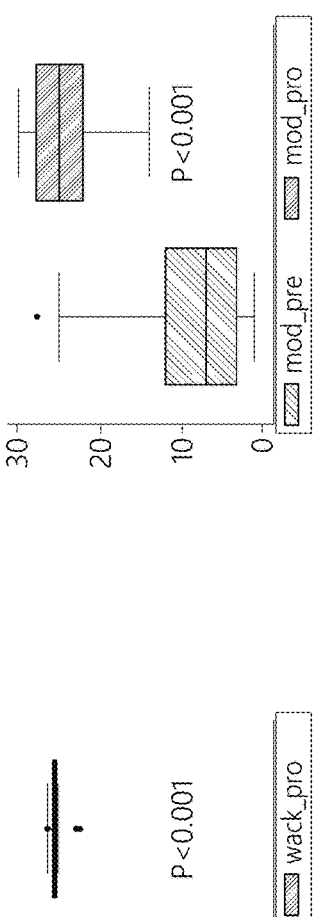

FIG. 7

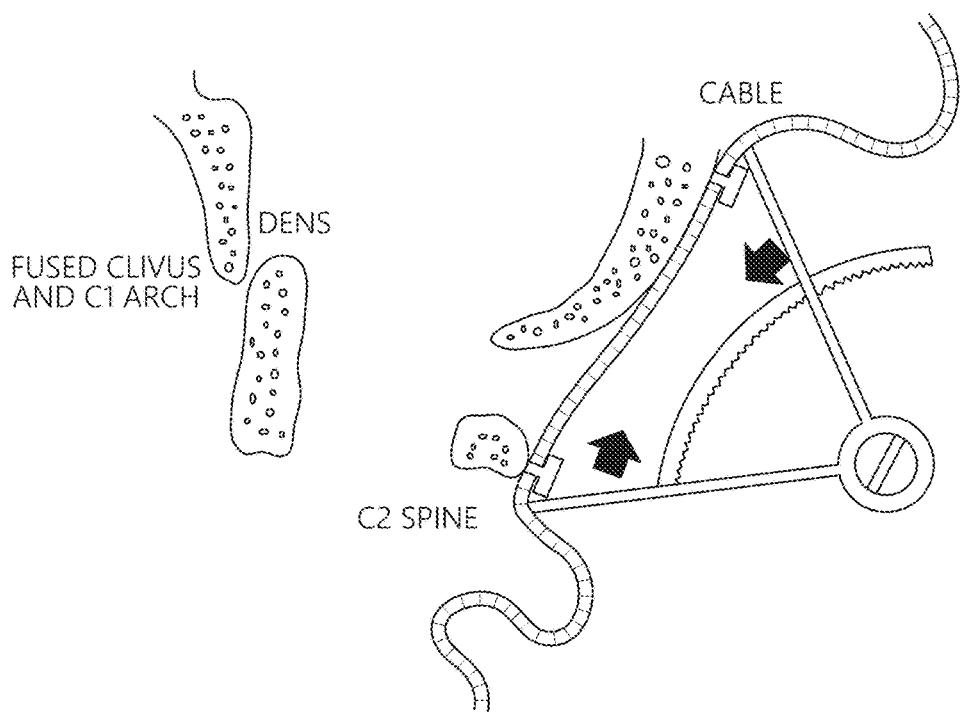
FIG. 10
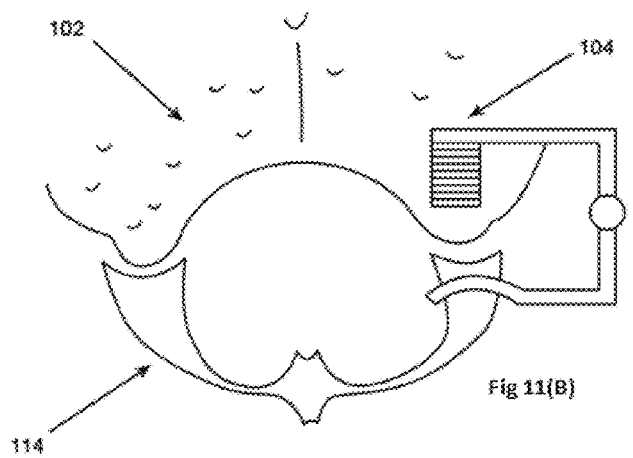
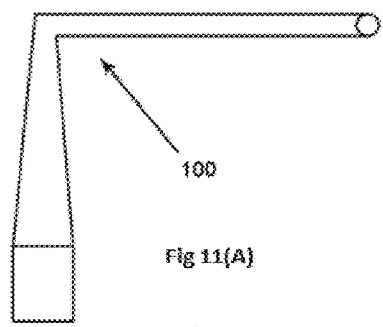
FIG. 11

FIG. 14
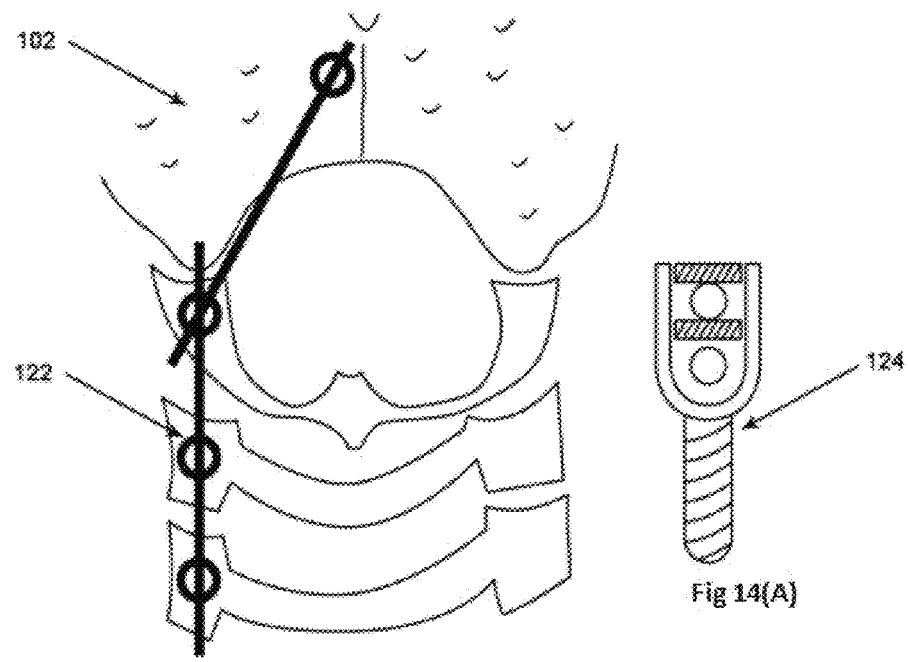
Fig 14(A)
Fig 14(B)
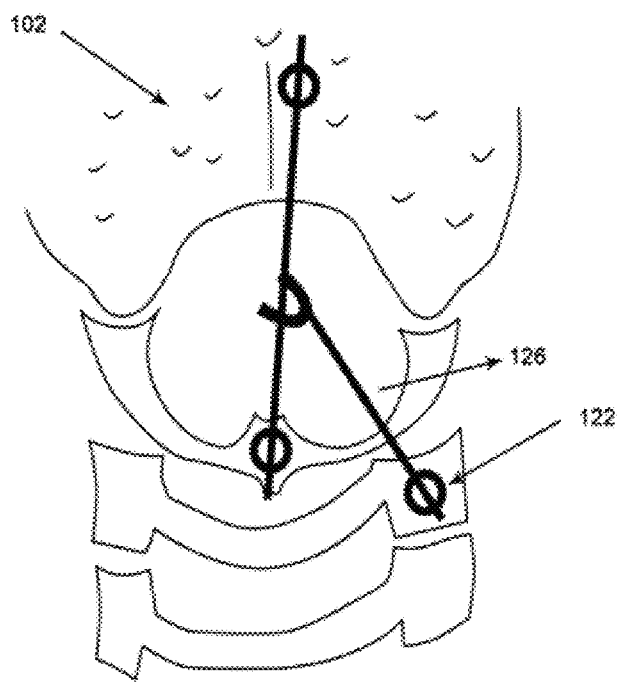
FIG. 15

TECHNIQUES FOR REDUCTION OF BASILAR INVAGINATION AND ATLANTO AXIAL DISLOCATION AND SURGICAL INSTRUMENTS THEREOF

CROSS REFERENCE TO RELATED APPLICATIONS

This application is a U.S. National Phase Application of PCT International Application Number PCT/IN2014/000385, filed on Jun. 9, 2014, designating the United States of America and published in the English language, which is an International Application of and claims the benefit of priority to Indian Patent Application No. 1724/DEL/2013, filed on Jun. 10, 2013, and Indian Application No. 1521/DEL/2014, filed on Jun. 6, 2014. The disclosures of the above-referenced applications are hereby expressly incorporated by reference in their entireties.

FIELD OF INVENTION

The present invention pertains to the field of neurosurgery and describes new methods to reduce basilar invagination (BI), and atlanto-axial dislocation (AAD). The invention further discloses novel surgical instruments useful in reducing basilar invagination (BI) and atlanto-axial dislocation (AAD).

BACKGROUND OF THE INVENTION

Management of basilar invagination (BI) and atlanto axial dislocation (AAD) is complex. The traditional paradigms for management included a trans oral excision of odontoid process followed by posterior instrumented fusion[1,2,3]. Wang et al suggested a trans-oral release of the ligaments around the odontoid process as the first stage of the treatment, followed by a posterior instrumented fixation in a second surgery.

Distraction of the C1-C2 joint has been recognized as an established form of treatment over the past decade[4,5]. Distraction of C1-C2 joint can effectively reduce the BI and also AAD to some extent. However the main shortcoming of distraction is that it can provide re-alignment in a vertical direction mostly and does not offer any movement in the horizontal axis.

Jian et al introduced a concept of intra-operative distraction cases of BI with assimilated C1 arch, where a rod was connected to C2 pedicular screw and occipital screw following, which distraction was performed reducing both BI and AAD. They achieved satisfactory results. However, the shortcoming of this procedure was that, it could provide distraction only as a method of reduction for both AAD and BI. AAD for its optimal reduction also requires a forward movement of dens as compared to BI, which requires only a vertical distraction. This is reflected in their results, where BI could be reduced in almost all patients but the AAD could be reduced completely in only 85% of their cases. In addition, distraction only without a spacer placement carries a risk of re-settling, this also was reflected in some of their cases.

Hsu W et al overcome this shortcoming by describing a novel technique in 2 cases of acquired (one infection and other in metastasis) occipito-cervical instability. Here, apart from intra-operative occipiti-cervical distraction, they also provided an extension of neck by applying compression between the upper occipital screw and another screw tightened more superiorly on the rod, which technique clearly demonstrated that while distraction corrects BI, extension while maintaining distraction results in correction of AAD. Distraction was performed without a spacer followed by extension that was provided by compressing 2 cranial screws. The latter technique while useful in acquired destructive pathologies (like malignancies) of craniovertebral junction may be difficult in developmental anomalies with more rigid joints. In addition, resettling may occur over a period of time due attrition at the bone screw interface.

In the Sonntag technique, a sublaminar cable is passed under the posterior C1 arch from inferior to superior. Next a notched iliac crest is placed in between the spinous process of C2 and wedged underneath the posterior arch of C1. Both the superior aspect of the C2 spinous process and the inferior arch of C1 are decorticated before graft placement. The cable is then looped over the iliac crest autograft and placed into a notch created on the inferior aspect of the C2 spinous process. The cable is then tightened and crimped.

The disadvantage of this method involves the use of a halo to immobilize patients for three months after surgery and the use of a rigid cervical collar for an additional one to two months after that. Neurological complication including quadriparesis can occur in up to 5 to 7% of cases and breakage of wire might occur.

The technique of segmental atlantoaxial fixation and fusion using C1 lateral mass screw and C2 pedicle screw and plates was pioneered by Prof Goel et al. The main drawback of this procedure is that only vertical distraction (which corrects BI) is provided in this technique and no horizontal corrective motion is provided for in this technique, which would be required to correct the AAD. In addition, C1 lateral mass screws joined with C2 pars screws while providing stabilization, may not provide enough forces to resist any intra-operative manipulation that may be carried out in view of the short lever arm with respect to the fulcrum. The procedure is technically demanding and precise and an exact three-dimensional understanding of the anatomy of the region and of the vertebral artery is mandatory. Large venous plexuses in the lateral glutter need to be handled appropriately.

SUMMARY OF THE INVENTION

The present invention, in one embodiment provides a novel technique, whereby intraoperative manipulation involving both distraction, followed by compression and extension performed over a fulcrum provided by a joint spacer results in reduction in both BI and AAD. The technique provides for movements in both vertical and horizontal directions, hence caters to correction of both BI and AAD. The technique is based on standard principles of lever mechanics, hence reduces the bone screw interface tension by providing a longer lever arm. This technique is safe, effective, less time consuming and avoids a trans-oral procedure in most of the cases. The underlying principle of treatment is not just to relief the compression but also to provide optimal stability and correction of deformity. The technique utilizes a spacer to convert the craniovertebral junction joint into a type II pivot joint so as to produce an additional movement in the horizontal direction to reduce the AAD. The technique is termed distraction, compression and extension reduction (DCER).

In another embodiment, the present invention provides the technique of dynamic distraction coupled with cable compression which overcomes some of the shortcomings of procedures like DCER or in cases where DCER cannot be performed at all.

Though DCER is more effective than the earlier known surgical techniques to produce a movement in the horizontal direction, it does not allow the correction of posterior subluxation of the C2 joint in the saggital axis (FIG. 8). Dynamic distraction coupled with cable compression (DDCC) is a technique, which overcomes this shortcoming. By a combination of distraction, while compressing the posterior elements using a cable, it distracts and reduces the C1/C2 joint subluxation first. This allows for a proper placement of a spacer to allow an effective DCER to be performed.

The DDCC technique may be especially used in:
1. Patients with saggital C2/C1 joint subluxation: In this case DDCC is performed followed by DCER
2. Patients with vertically oriented joints where a DCER cannot be performed.

The present invention also provides surgical, instruments for successfully executing the DCER and DDCC surgeries.

The object of the invention is to develop a novel new technique for intra-operatively correcting both Basilar Invagination (BI) and Atlanto-Axial Dislocation (AAD) using distraction, compression and extension reduction (DCER) performed over a fulcrum provided by a joint spacer.

Another object of the invention is to develop a novel new technique for intra-operatively correcting both Basilar Invagination (BI) and Atlanto-Axial Dislocation (AAD) using dynamic distraction coupled with cable compression (DDCC).

Another object of the invention is to provide techniques which are safe, effective, less time consuming and avoid a trans-oral procedure in most of the cases.

Yet another object of the invention is to bypass the two stage procedure of anterior transoral surgery and posterior fixation together for the treatment of BI with AAD.

Yet another object of the invention is to bring down steep learning curve, high morbidity and high mortality associated with transoral surgery.

Further object of the invention is to develop methods for the treatment of BI and AAD, which involve a standard and structured procedure that is reproducible and increase the safety of patients.

Another object of the invention is to provide novel surgical instruments for performing DCER and DDCC.

BRIEF DESCRIPTION OF THE DRAWINGS

A further understanding of the present subject matter can be obtained by reference to various embodiments set forth in the illustrations of the accompanying drawings. The drawings are not intended to limit the scope of the present subject matter, which is set forth with particularity in the claims as appended or as subsequently amended, but merely to clarify and exemplify the subject matter.

For a more complete understanding of the present subject matter, reference is now made to the following drawings in which:

FIG. 3: The following schematic figure shows the mechanical advantage of the described procedure. FIG. 3a=represents the conventional procedure as described by Goel et al. FIG. 3b shows fixation between C1 (using lateral mass) and C2 (using trans laminar screw). FIG. 3c depicts the occipito-C2 (trans-laminar) fixation in cases where the C1 is fused with occiput in developmental cranio vertebral junction anomalies. F is the force transmitted to the bone. As it can be seen here, the model depicted is a Class II lever (with the pivot in the center). FC represents the compressive force thrust by the implants through the screws into the bone. This is a function related to the length of the lever arm measured from the pivot or fulcrum to the point of attachment of implant (in this case L and M). FD represents the distractive force thrust by the spacer, required to overcome the tissue resistance, and is a function of the lever arm N and O i.e. the distance from the anterior margin of C1 and C2 bodies till the fulcrum (center of spacer: e). As it can be seen here, the lever arms N and O remains constant in all 3 techniques, while the lever arms L and M varies depending on the technique. Thus FD is constant in all the 3 technique, while FC may be modified depending on the length of lever. Ideally FC should be greater than FD to maintain optimal stability and reduced alignment, but not so much that it would cut through the bone. It can be, seen that with increase of the length of the lever arms L and M, the FC will reduce (FIG. 3b and FIG. 3c). Thus the amount of force transmitted to the bone through the screw will reduce, increasing the chances of better long term screw purchase; Here it can be seen that in procedures described by the author i.e. C1 lateral mass/C2 translaminar and C2 trans-laminar/occiput implant fixation (FIGS. 3b and 3c) results longer lever arms (L, M) as compared with the conventional Goel & Harms technique (FIG. 3a). Thus the forces transmitted to the screws is proportionately less. This may lead to a better long term bone purchase and fusion rates. It may be also of greater advantage for maintaining alignment especially following the reduction technique described here.

FIG. 4: The following figure demonstrates the mechanical advantage of combining a trans laminar screw with a C1 lateral mass screw. In addition to providing a longer lever arm, as has been explained in FIG. 3, it provides a better mechanical advantage to reduce the AAD (pre-op: FIGS. 4c & post-op: 4d) by creating a torque (arrows, FIG. 4b). The direction of the trans-laminar screws also helps to provide this advantage, i.e. one screw passing from a superior to inferior direction and the other screw passing from inferior to superior direction.

FIG. 6: A 21 year old female patient, with severe basilar invagination and atlanto-axial dislocation (FIG. 6a) presented with progressive myelopathy. MRI showed evidence of long segment syringomyelia (FIG. 6b). Following occipital-C2 DCER, both BI and AAD were corrected (6d). Post operative MRI performed at 3 months revealed significant resolution of the srynigomyelia. Patient symptoms also improved significantly from Nurick's grade IV to grade II.

FIG. 7: The following figures demonstrate correction of various radiological parameters

FIG. 10: The figure shows the manner by which the cable may be used. The cable is fixed by tightening it over the screws placed over occiput or the C2 spine. A separate caliper is used to compress the occiput and C2 spine and then tightening the screw to hold the cable in place. Further cable compression may be performed after Step III. This allows further reduction of AAD, after complete reduction of BI by allowing further movement in the horizontal direction.

FIGS. 11(A) & 11(B): is a schematic representation of joint distractor and its arrangement with the occiput respectively; and is in accordance with an embodiment of the present subject matter.

FIGS. 14A & 14B is a schematic representation of a double headed screw and its arrangement with the occiput respectively; and is in accordance with an embodiment of the present subject matter.

FIG. 15 is a schematic representation of C2-occiput rod and C3 lateral mass screw connector in accordance with an embodiment of the present subject matter.

DETAILED DESCRIPTION OF THE INVENTION

Distraction, Compression and Extensive Reduction (DCER)

Figure 1:
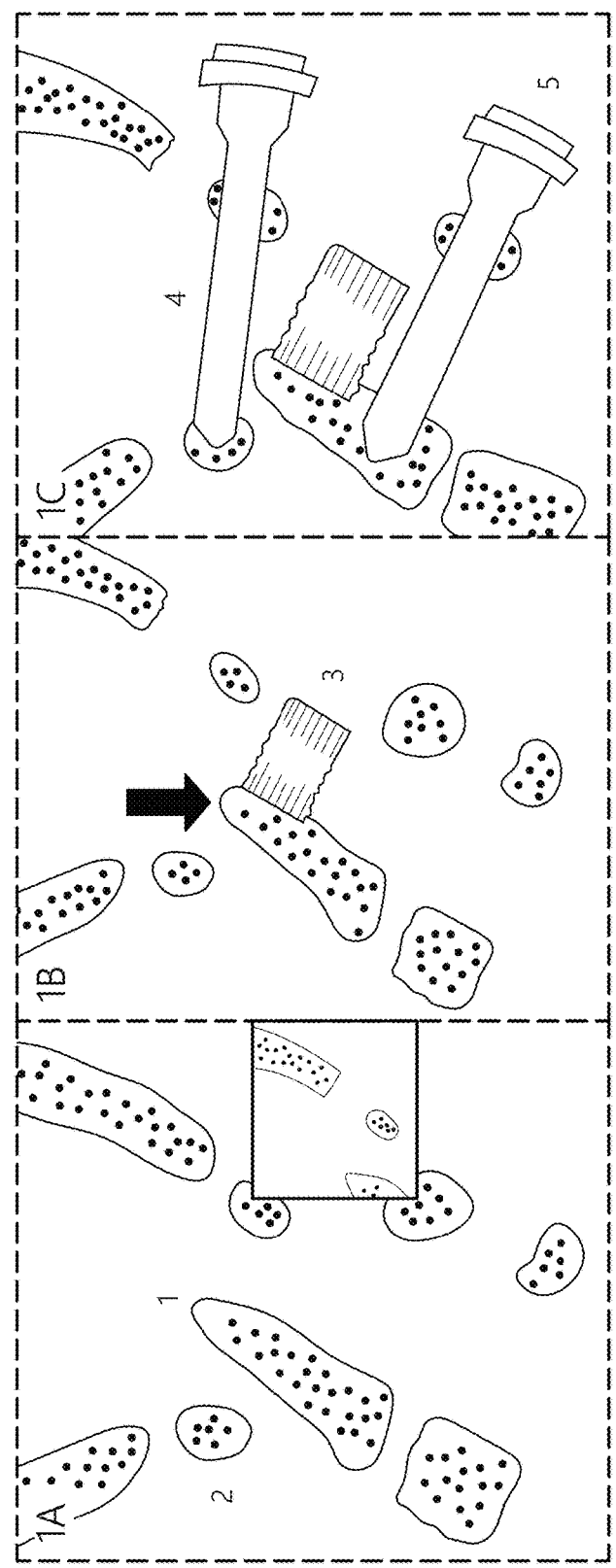
FIG. 1: Schematic diagrams demonstrating step by step procedure in a patient with basilar invagination (BI) and atlanto axial dislocation (AAD), where the C1 arch is not assimilated (FIG. 1a). Step I: The posterior margin of the foramen magnum is drilled (inset, FIG. 1a). Step II (Distraction): The spacers are now placed bilaterally (FIG. 1b). This results in correction of BI (down arrow) but not AAD. C1 lateral mass screws and C2 trans-laminar screws are next placed (FIG. 1c). An offset connected to a laminar clamp is then placed over C1 arch (FIG. 1e). Step III (Compression and extension): Compression is next performed. This is done by placing the arms of the instrument over the offset superiorly and under the laminar screws inferiorly (FIGS. 1d, 1e, & 1f). This results reduction of the AAD by moving the tip of the dens anteriorly (horizontal arrow, FIG. 1d) by converting the spacer into a Type II pivot joint (large dot, FIG. 2d).
Figure 1:
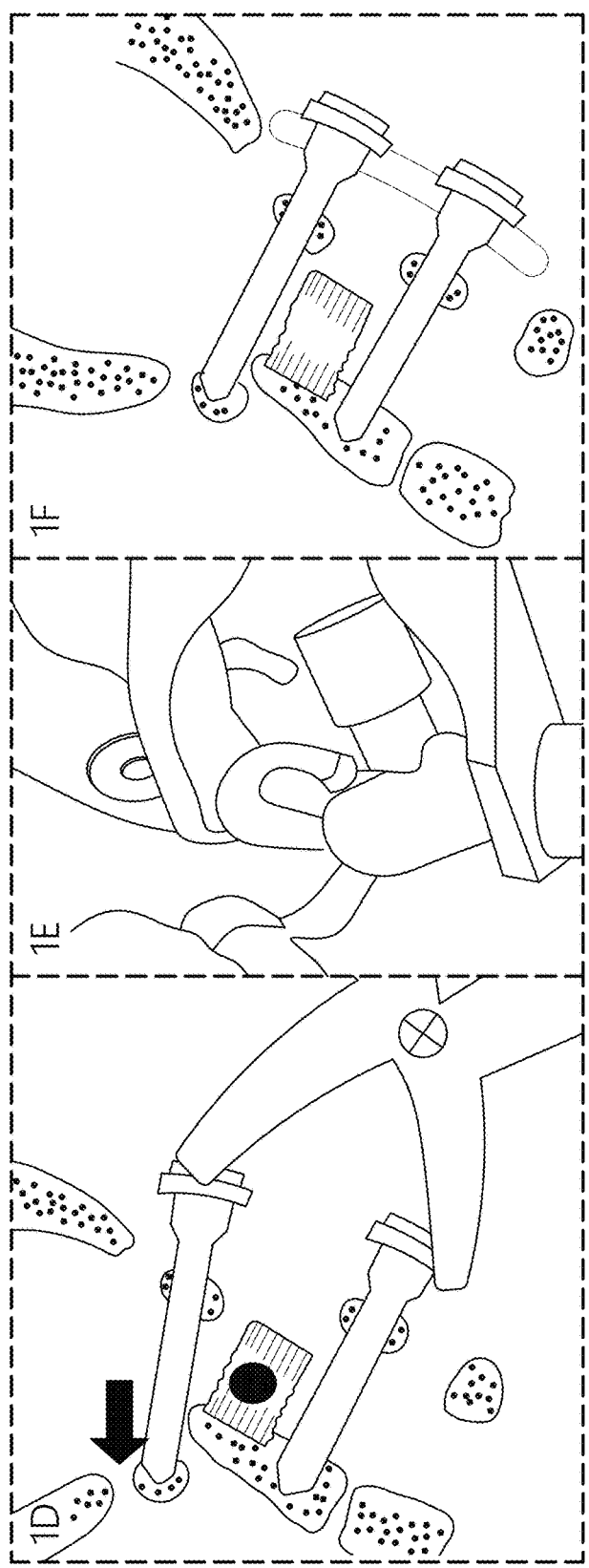

The present invention, in one embodiment, discloses a novel technique, whereby intraoperative manipulation involving distraction, followed by compression and extension is performed over a fulcrum provided by a joint spacer which results in reduction in both BI and AAD.

The present invention provides a novel technique, wherein the spacers are first used to distract the joint to correct the BI and then as a fulcrum over which simultaneous compression and extension was provided to correct the AAD. Since the procedure involves movements of distraction, compression and extension, it is called Distraction, Compression and Extensive Reduction (DCER). The present technique first uses a spacer followed by extension using the spacer as a pivot.

Thirty five patients (May, 2010-April, 2012), who had basilar invagination (BI) with atlanto-axial dislocation were operated. Of these, 24 patients have had a follow up of 1 year and above.

Surgical Procedure

Distraction, compression and extensive reduction (DCER) was performed in all patients with BI and AAD. There was no need to perform trans-oral procedure in any of the patient. All patients underwent a placement of overnight cervical skeletal traction (Gardner Wells)

All patients underwent, awake endoscopic intubation without any manipulation of the neck. Following general anesthesia, the patient was placed in the prone position on a U shaped headrest with the head fixed on the skeletal traction and the neck in neutral position. Using a standard midline skin incision, the occipital squama, the posterior edge of the foramen magnum and the C2 spinous process was exposed. From here onwards, the procedure slightly differed depending whether the C1 was assimilated or not. However, the principle of the surgical procedure remained same and consisted of 3 steps i.e.

1. Removal of posterior margin of the foramen magnum
2. Distraction and placement of a spacer leading to vertical reduction of BI
3. Compression and extension C1 or C1/occipital complex over C2 over the fulcrum created by placement of the spacer leading to reduction of AAD.

Since the procedure involved all 3 movements, i.e. distraction, compression combined with extension, this was named as distraction, compression and extension reduction. A detailed description is provided below.

The current procedure may be of a greater advantage than other procedures that involve just distraction or distraction combined with extension without a mechanical support of a spacer, which would then act both like a pivot and a channel for weight distribution. DCER is fundamentally based on the principle of (1) using a spacer as a fulcrum to correct the AAD and BI more effectively, all through a posterior approach only, and (2) may also provide a better biomechanical long term stability due a better support both by the spacer ventrally and the construct placed dorsally (3) presence of a longer lever arm may provide a longer retention of the construct due to reduced bone/screw strain.

Procedure in Patients where the C1 Arch was not Assimilated with Occiput (FIG. 1)

The posterior margin of the foramen magnum was drilled first. Dural bands if present were released. The main purpose of this was to provide for cord expansion and also to allow placement of the C1 laminar hook over the C1 arch while performing compressive extension. A distractor with tips of the blade was now kept between C1 and C1 posterior arches and very gently distracted to open up bilateral joint spaces. The joint capsule was widely opened. The C2 nerve root was routinely cut to create space for placement of the spacer. The cartilage over the joint was drilled using a fine diamond drill to expose the cortical bone. Next the size of the spacer was determined. This corresponded to the length of basilar invagination and usually was around 5-6 mm. once the joint space was prepared, PEEK (Polyether ether ketone, Globus medical, USA) spacers were placed bilaterally. The C1 and C2 joint spaces were opened on both the sides as per standard Goel's technique. This resulted in correction of BI by vertical distraction. This was followed by placement of C1 lateral mass screws. Following this (3.5 mm, diameter) C2 trans-laminar screws were placed. The lengths of C2 trans-laminar screws varied from 26-32 mm hence providing a secure and rigid fixation. Next a cervical laminar clamp attached to an offset was passed over the upper border of C1 arch (Globus medical, USA). Following this, compression was provided with the tips of the blades placed superiorly between the offset and the laminar clamp and inferiorly below the C2 screw (FIG. 1). As can be noted from FIG. 1, distraction provided reduction of the BI, while compression along with extension after placement of spacers (which now acted as a fulcrum in a type II lever) resulted in a forward movement of the odontoid process and reduction of AAD. In addition, as can be seen from FIG. 3, a trans-laminar screw provides a longer lever arm thus reducing the screw bone tension. Thus the amount of force transmitted into the C2 bone may be less, thus providing a better chance of long-term screw retention as compared to C2 pedicular screw. C2 trans-laminar screws also forms a torque with C1 lateral mass screws (FIG. 2), thus resulting in a better horizontal compressive force along with a vertical compressive force as well.c2 trans-laminar/c1 lateral mass screws along with a spacer form a stable construct and serve an ideal model for DCER in cases where C1 arch was not assimilated. The entire procedure was performed under fluoroscopy guidance.

Figure 2:
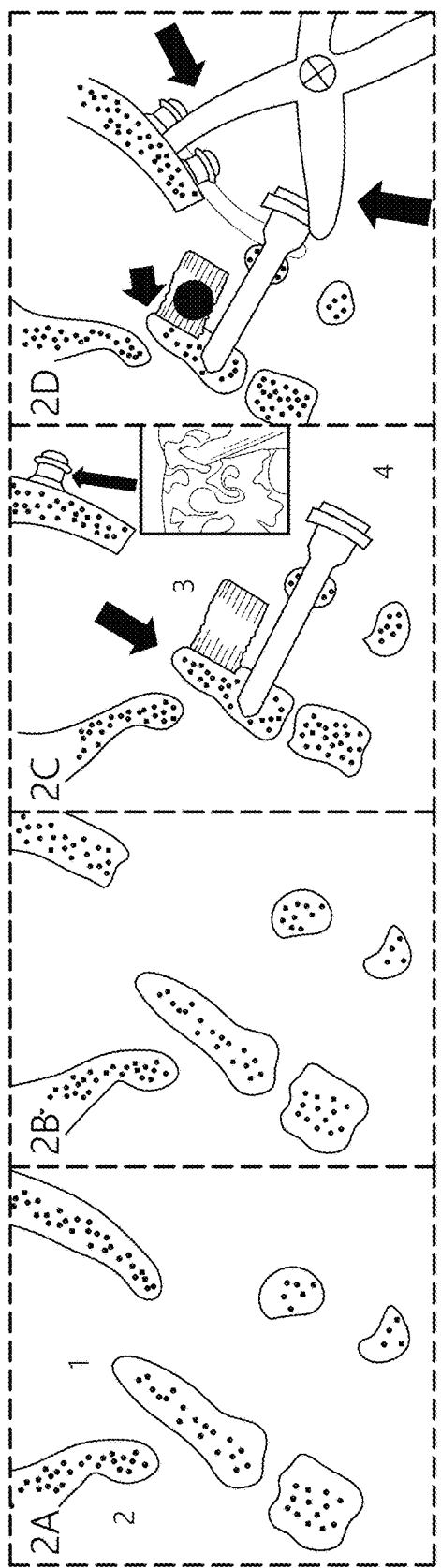
FIG. 2: Schematic diagrams demonstrating step by step procedure in a patient with BI and AAD, where the C1 arch was assimilated with the occiput (FIG. 1a). Step I: The posterior margin of the foramen magnum is drilled (FIG. 1b). Step II (Distraction): The spacers are now placed bilaterally (FIGS. 2a, 2b, 2c, & 2d). This again results in correction of BI but not AAD (down arrow, FIG. 2c). The C2 trans-laminar screws are next placed followed by placement of a temporary occipital screw (FIG. 2f). This is now attached to an offset, which acts as one of the holding points for the compressor (inset and up arrow, FIG. 2c). Step III (Compression and extension): Compression is next performed. This is performed by placing one arms of the compressor over the offset (attached to the temporary occipital screw) superiorly and below the trans-laminar screw inferiorly (FIG. 2d, 2i). While the assistant maintains the compression (FIG. 2g), the surgeon fixes the rod to the trans laminar screw below and to a occipital screw above. This results in correction of AAD by anterior movement of the dens due to the pivot created by the spacer (forward arrow, large dot, FIG. 2d). Thus correction of BI and AAD are achieved by this technique (FIG. 2e, 2h).
Figure 2:
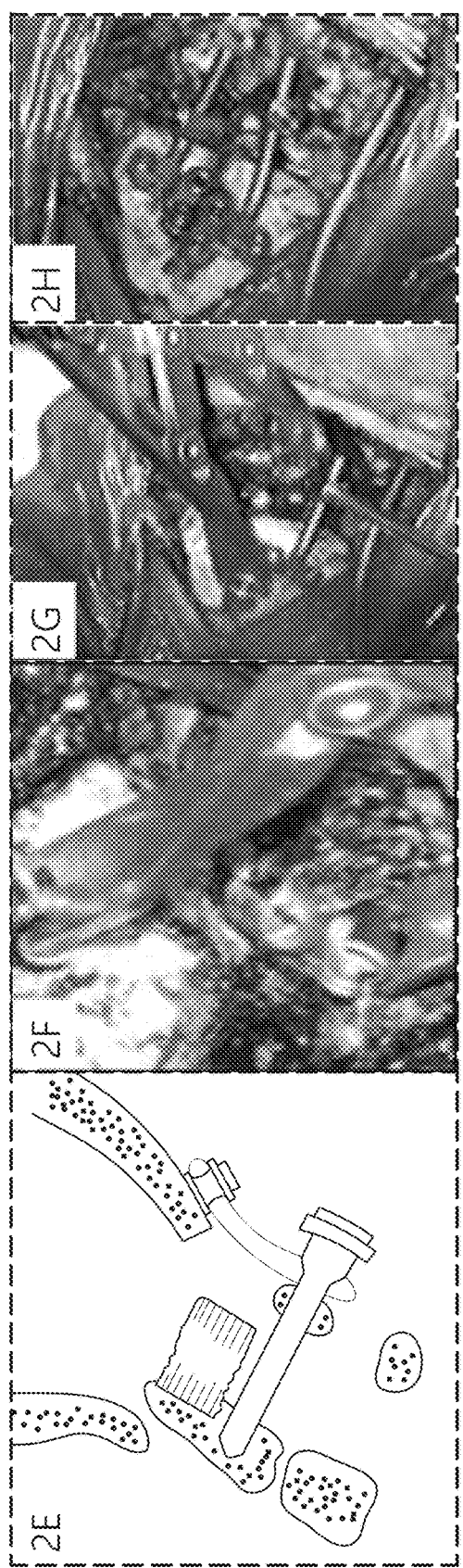
Figure 5:
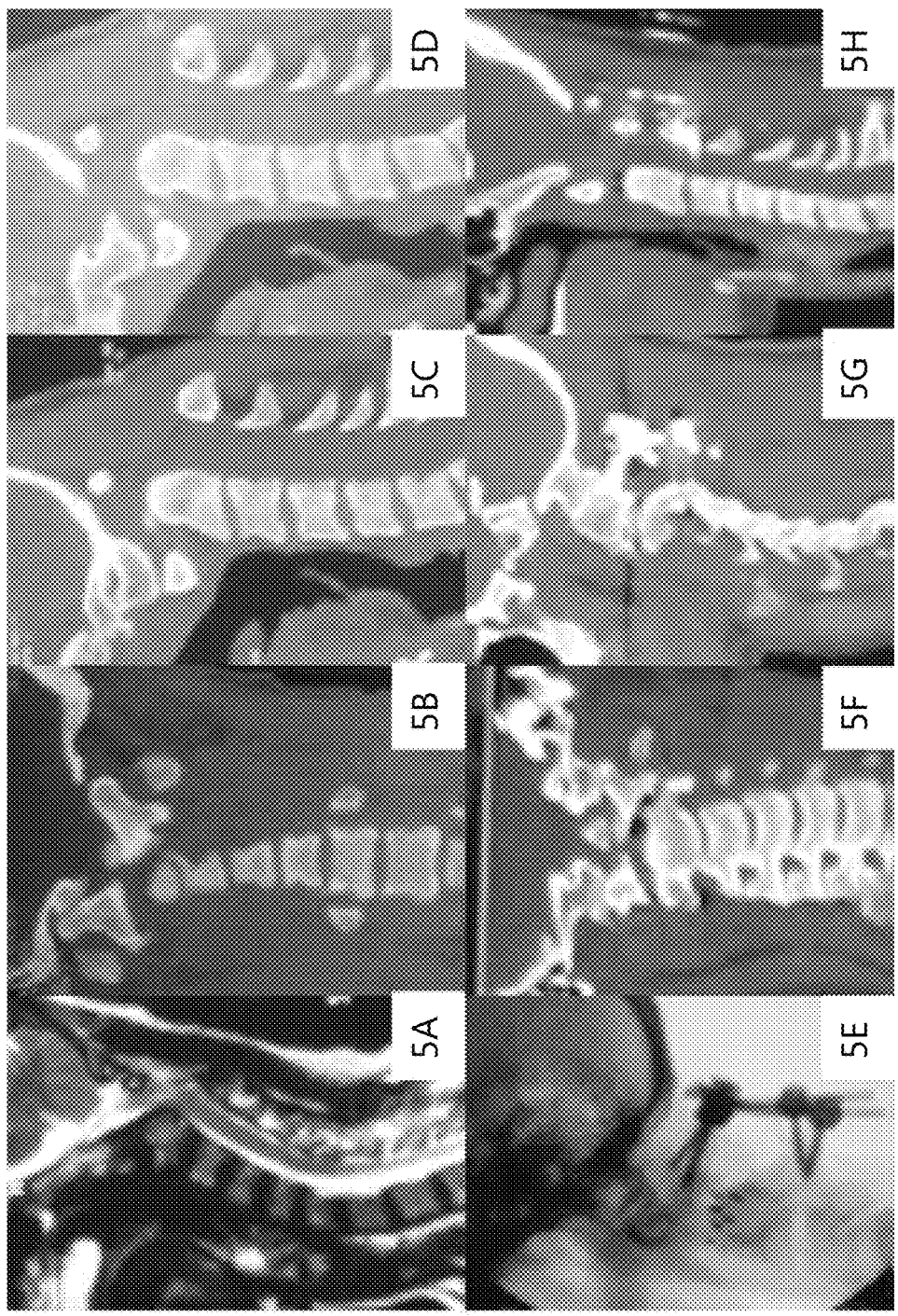
FIG. 5: A 33 year male patient presented with severe compressive myelopathy. There was a history of fall from height, when he was about 19 years of age. MRI showed evidence of atlanto axial dislocation with severe compression of the cord (5a). CT scan, coronal images (5b) showed severely rotated and dislocated dens with atlanto-axial dislocation (FIGS. 5c & 5d). Patient underwent distinctive compressive reduction with C1 lateral mass screw and C2 frans-laminar screw placement (FIGS. 5c and 5e). Following surgery, the position of the dens was restored to the midline (FIG. 5f and FIG. 5g) and normal alignment was restored (FIG. 5h).

Patients where C1 Arch was Assimilated with Occiput (FIG. 2):

Here the margin of posterior rim of foramen magnum is drilled first. Following this the joint spaces bilaterally were opened up. To facilitate the opening of joining spaces, the arms of the distractor were placed between the occiput superiorly and the upper border of the C2 inferiorly. The size of spacers are measured and placed within the joint space on both the sides. As shown in FIG. 2, spacer placement results in correction on BI but not AAD. Following this, the C2 trans-laminar screws are inserted and a temporary screw was placed on the occiput. An offset (Globus medical, USA inset picture between FIG. 2c) was now connected to the occipital screw head. A compressor was next placed with one of the arm over the gap between the offset and the screw superiorly and the other below the C2 trans-laminar inferiorly. Gentle compression was applied. The spacer now acted as a fulcrum of a type II lever (FIGS. 2 & 3). The resultant movement caused both compression and extension and lead to reduction of AAD. The entire procedure was performed under fluoroscopy guidance. While the assistant maintained the compression, occipito-cervical rod was placed on one side and fixed (FIG. 2g). Following this the compressor was removed and similar fixation was also performed on the other side (see also FIG. 6).

In cases, where the C1 arch was not assimilated, an occipital and C2 trans-laminar screws were used (FIG. 4, 5 as they provided long lever arms (FIG. 3) thus once again reducing the amount of force being transmitted into the bone.

Following surgery, the exposed cortical occipital and C2 spinous bone was decorticated using a fine diamond drill. Bone chips harvested from iliac crest mixed with hydroxylapatite was placed between the occiput and C2 spinous process. Wound was closed in layers. Drain was placed if felt necessary.

All patients were electively ventilated overnight and slowly weaned off the ventilator and extubated the next day. Patients were advised Philadelphia hard cervical collar for the next 6-9 months till bone fusion was demonstrated.

Results

Surgery

Occipital-C2 DCER was performed in 28 patients (26 patients with assimilated C1 arch, and 2 patients where the C1 arch was very thin or broken during procedure, hence a Oc-C2 DCER was performed). C1/C2 DCER was performed in 3 patients. C2 laminae was found in all cases and the thickness varied from 4.3-5.6 mm. the length of C2 laminar screws varied from 26-32 mm. the duration of the operation ranged from 80 to 190 minutes (mean 110±24 minutes), and blood loss ranged from 90 to 500 ml (mean: 170±35 ml).

Clinical Outcome

There was no postoperative neurological deterioration or swallowing difficulties. Thirty-two of 35 (94%) improved clinically and 2 patients (5%) had symptoms. A total of 24 patients were included for long term evaluation with atleast 1 year follows up (table 2). This mean follow in these 24 patients was 19.75±7.09 with a range of 12-39 months (median: 18 months); the mean post-operative Nurick's score 1 year improved significantly after surgery and was 1.3±0.53, compared with a mean pre-operative score of 3.3±0.63 (P<0.001). (Table2).

There was 1 death after surgery in this series. The patient had long standing hypertension and underwent a cardiac bypass 4 years ago. During surgery 9 while dissecting the cervical superficial muscles), he had a sudden fall of blood pressure along with T wave changes. This was corrected using appropriate measures that included simultaneous dobutamine and dopamine infusion. The blood pressure was corrected, but following surgery, the patient did not regain consciousness although he was moving limbs on both sides spontaneously. He was electively ventilated. CT scan showed multiple infarcts in the watershed areas and also in the posterior fossa. He did not improve, continued to have fluctuating blood pressure and died on the 5th post-operative day.

One patient developed severe wound infection. This was treated with appropriate injectable antibiotics along with meticulous dressings. The wound healed gradually over 8 weeks with healthy granulation and a large scar. In one patient, the spacer slipped forward from the joint space and could not be retrieved. Hence it was left in-situ and a fresh spacer was placed. 1 patient complained of persistent numbness of right upper limb. Both CT and MRI showed both construct and spacer in situ.

Radiologic Follow-Up

X-ray and CT scans were performed at 1 week, 3 months, and 6 months to 1 year after surgery. They were performed until bone fusion was confirmed. Bone fusion was commented in only those cases with at least 1 year of follow up (n=24), Table 2.

MRI follow-up was done, 3 months later, during the follow-up period. Table 3 shows the pre- and postoperative radiologic measurements. Compared with the preoperative parameters, the ADI became normal (0 or 1 mm) in 33 patients (94%), demonstrating complete correction of the atlanto-dental interval.

Reduction was not complete but was more than 50% in 2 patients (6%). The mean post-operative distance of the dens below the McRae's line was 2.8±1.7 mm as compared to the mean pre-operative distance of 10.8±5.8 mm above the McRae's line. McRae line reached value normal in 8 patients (reaching to a value of 4.2 mm below this line. Similarly all other parameters showed significant improvement (CL: mean pre op value of 11±6.7 mm above the line as compared to mean post op of 2.3±1.9 mm below the line; WL: mean pre op value 8.2±3.4 mm above the line as compared to a mean post op value of 1.2±0.6 mm below the line; CCA: mean pre op angle of 116±19 deg as compared to an improvement to a mean post op angle of 149±8 deg; RL: mean pre op distance was 8.7±6.9 mm increasing to a distance of 24±18 mm following surgery). The improvement in all radiological parameters were significant (FIG. 7; p<0.001)

CT with saggital reconstruction and MRI showed good decompression of the spinal cord and medulla oblongata during follow-up in all 35 patients (100%), by relief of compression or opening up of the subarachnoidal spaces around the foramen magnum. Shrinkage of the syrinx, was seen in all 7 patients. Repeat CT scans of all patients did not show any evidence of further settling after 3 months and the construct was found stable in all post operative images.

Fusion was considered to have occurred when the CT scan showed a bridging bone mass formation and a dynamic x-ray showed a stable reduction of the dislocation without failure of the implant 3 to 6 months after surgery. If the bone mass was not present on x-ray 3 to 6 months after surgery, the patient had another x-ray or CT scan 6 months to 1 year postoperatively. Solid fusion was found in 24 patients at 5 to 15 months (mean 7.2±3.1 months) (Table 2). Bone fusion was not commented in 11 patients, as the period of surgery was less than 6 months.

TABLE 1

Clinical profile of 35 patients with basilar invagination and atlanto-axial dislocation*:

| Clinical features | No. of patients (%) |
|---|---|
| Quadriparesis | 33(96%) |
| Neck pain | 21(62%) |
| Unsteady gait | 18(52%) |
| Short neck, low set ears | 11(32%) |
| Numbness of limbs | 8(22%) |
| Torticollis | 5(14%) |
| Hemiparesis | 3(8%) |
| Respiratory difficulty | 2(5%) |

*One patient may have more than 1 clinical feature

TABLE 2

Associated Radiologic Anomalies, Surgery performed, Clinical Outcomes, and Radiologic Follow-up

| S. No | Age | Sex | Radiology | Surg | Nurick's Grading* Pre-op | Nurick's Grading* Post-op | Bone fusion confirmed mo | Follow up mo (12-39) |
|---|---|---|---|---|---|---|---|---|
| 1 | 24 | F | C1A | Oc-C2 | 4 | 1 | 6 | 39 |
| 2 | 36 | F | C1A | Oc-C2 | 3 | 1 | 5 | 36 |
| 3 | 15 | F | C1A | Oc-C2 | 4 | 2 | 15 | 28 |
| 4 | 32 | M | C1A | Oc-C2 | 4 | 2 | 6 | 27 |
| 5 | 24 | F | C1A, Ch, Syr | Oc-C2 | 3 | 2 | 5 | 25 |
| 6 | 33 | M | C1NA | C1/C2 | 4 | 1 | 14 | 22 |
| 7 | 16 | F | C1A, Ch, Syr | Oc-C2 | 4 | 1 | 14 | 21 |
| 8 | 32 | M | C1NA | C1/C2 | 4 | 2 | 5 | 21 |
| 9 | 29 | M | C1A | Oc-C2 | 3 | 1 | 5 | 21 |
| 10 | 33 | F | C1NA | Oc-C2 | 3 | 1 | 6 | 20 |
| 11 | 12 | M | C1A | Oc-C2 | 4 | 1 | 5 | 19 |
| 12 | 13 | F | C1A, Ch, Syr | Oc-C2 | 3 | 1 | 6 | 18 |
| 13 | 13 | F | C1A | Oc-C2 | 3 | 2 | 4 | 18 |
| 14 | 21 | M | C1NA | C1/C2 | 4 | 3 | 6 | 18 |
| 15 | 12 | M | C1A, Ch, Syr | Oc-C2 | 3 | 1 | 12 | 17 |
| 16 | 15 | F | C1A | Oc-C2 | 2 | 1 | 6 | 16 |
| 17 | 43 | F | C1A | Oc-C2 | 2 | 1 | 6 | 16 |
| 18 | 14 | M | C1A, Ch, Syr | Oc-C2 | 3 | 1 | 8 | 15 |
| 19 | 18 | F | C1A | Oc-C2 | 3 | 2 | 7 | 15 |
| 20 | 68 | M | C1NA | Oc-C2 | 3 | 1 | 9 | 14 |
| 21 | 18 | M | C1A | Oc-C2 | 3 | 1 | 7 | 12 |
| 22 | 17 | F | C1A | Oc-C2 | 3 | 1 | 6 | 12 |
| 23 | 17 | M | C1NA | C1/C2 | 4 | 1 | 6 | 12 |

TABLE 2-continued

Associated Radiologic Anomalies, Surgery performed,
Clinical Outcomes, and Radiologic Follow-up

| S. No | Age | Sex | Radiology | Surg | Nurick's Grading* Pre-op | Nurick's Grading* Post-op | Bone fusion confirmed mo | Follow up mo (12-39) |
|---|---|---|---|---|---|---|---|---|
| 24 | 37 | M | C1NA | C1/C2 | 4 | 1 | 6 | 12 |
| 25 | 23 | M | C1NA | C1/C2 | 4 | 1 | NA | 9 |
| 26 | 30 | M | C1A | Oc-C2 | 5 | 1 | NA | 8 |
| 27 | 38 | M | C1A | Oc-C2 | 5 | 2 | NA | 8 |
| 28 | 16 | M | C1A | Oc-C2 | 5 | 2 | NA | 7 |
| 29 | 23 | M | C1A, Ch, Syr | Oc-C2 | 5 | 1 | NA | 7 |
| 30 | 38 | F | C1A | Oc-C2 | 5 | 3 | NA | 7 |
| 31 | 21 | M | C1A, Ch, Syr | Oc-C2 | 4 | 2 | NA | 7 |
| 32 | 48 | M | C1A | Oc-C2 | 5 | 2 | NA | 6 |
| 33 | 15 | M | C1A | Oc-C2 | 5 | 1 | NA | 6 |
| 34 | 12 | M | C1A | Oc-C2 | 4 | 2 | NA | 6 |

Abbreviations: Surg: Surgery; mo = months; m = male; f = female; C1A = C1 arch assimilated with occiput; C1NA = C1 arch not assimilated with occiput; Ch = Chiari malformation; Syr—Syringomyelia; Oc-C2 = occipito-C2 Distractive compressive reduction performed; C1/C2 = C1 and C2 Distractive compressive reduction performed. Blank cells in the 'Bone fusion' column indicates that the follow up was 6 months or less hence bone fusion could not be commented upon.
NA—not applicable, bone fusion was not commented upon for cases with less than 1 year of follow up
Nurick's grading: Grade 0: signs or symptoms of root involvement but without evidence of spinal cord disease; Grade 1: signs of spinal cord disease but no difficulty in walking; Grade 2: slight difficulty in walking which does not prevent full-time employment; Grade 3: difficulty in walking which prevented full time employment or the ability to do all housework, but which was not so severe as to require someone else's help to walk; Grade 4: able to walk only with someone else's help or with the aid of a frame; Grade 5: chair bound or bedridden.

TABLE 3

Pre and post operative radiological findings

| Pt. no. | Age | Sex | Atlanto Dental Interval, ADI (mm) Pre op | Atlanto Dental Interval, ADI (mm) Post op | Chamberlain Line, CL (normal = 2.3 ± 2.6 mm) Pre op | Chamberlain Line, CL (normal = 2.3 ± 2.6 mm) Post op | Mc Rae's Line, ML (normal = 5.8 ± 1.6 mm) Pre op | Mc Rae's Line, ML (normal = 5.8 ± 1.6 mm) Post op | Wackenheim Line, WL (normal = 0.9 ± 2.2 mm) Pre op | Wackenheim Line, WL (normal = 0.9 ± 2.2 mm) Post op | Clivus Canal Angle, CCA (Normal > 150 deg) Pre op | Clivus Canal Angle, CCA (Normal > 150 deg) Post op | Modified Ranawat's Line, RL (Normal value: 29.7 ± 2.6 mm) Pre op | Modified Ranawat's Line, RL (Normal value: 29.7 ± 2.6 mm) Post op |
|---|---|---|---|---|---|---|---|---|---|---|---|---|---|---|
| 1. | 24 | F | 4 | 2 | −5 | 1.2 | −3 | 3.2 | −6.4 | 1 | 100 | 145 | 3 | 18 |
| 2. | 36 | F | 4 | 1 | −4.3 | 1.8 | −5 | 4.3 | −6.4 | 1.2 | 92 | 144 | 11 | 14 |
| 3. | 15 | F | 5 | 0 | −3.9 | 5 | −2.4 | 3.1 | −5.4 | 1.1 | 140 | 150 | 8 | 16 |
| 4. | 32 | M | 5 | 0 | −2.7 | 1.8 | −3.5 | 2.3 | −6.5 | 1.9 | 160 | 155 | 17 | 18 |
| 5. | 24 | F | 4 | 0 | −2.9 | 1.9 | −4.5 | 3.7 | −3.2 | 1.3 | 120 | 140 | 3 | 19 |
| 6. | 33 | M | 4 | 1 | −3.2 | 2.9 | −3.2 | 4.5 | −3.6 | 1.1 | 155 | 160 | 7 | 17 |
| 7. | 16 | F | 5 | 0 | −6.1 | 3 | −5.6 | 3.2 | −4.3 | 1.2 | 99 | 139 | 12 | 25 |
| 8. | 32 | M | 6 | 1 | −23 | −2 | −19.3 | 1.1 | −7.9 | 1.1 | 140 | 140 | 17 | 26 |
| 9. | 29 | M | 7 | 1 | −34 | −4 | −25.7 | −1.3 | −11.3 | 1.2 | 120 | 155 | 20 | 22 |
| 10. | 33 | F | 6 | 1 | −14 | −1.4 | −16.2 | −1.8 | −12.2 | 1.1 | 92 | 130 | 12 | 22 |
| 11. | 12 | M | 7 | 2 | −16 | 2.4 | −12.3 | −2.3 | −9.7 | 1.4 | 100 | 135 | 25 | 30 |
| 12. | 13 | F | 5 | 1 | −12 | −1.4 | −10.2 | 2.9 | −9.3 | 1.5 | 105 | 138 | 19 | 26 |
| 13. | 13 | F | 6 | 0 | −8.2 | 2.3 | −7.6 | 2.4 | −5.4 | 1 | 115 | 150 | 10 | 28 |
| 14. | 21 | M | 5 | 0 | −8.9 | 3.2 | −7.4 | 1.7 | −5.7 | 2.3 | 105 | 156 | 1 | 29 |
| 15. | 12 | M | 6 | 0 | −9.2 | 4.8 | −7.4 | 4.9 | −6.5 | 2.1 | 110 | 138 | 10 | 30 |
| 16. | 15 | F | 5 | 1 | −8.4 | 2.3 | −9.7 | 5.3 | −7.6 | 1 | 115 | 157 | 3 | 24 |
| 17. | 43 | F | 6 | 0 | −8.1 | 2.1 | −8.6 | 4.3 | −7.6 | 1.1 | 130 | 156 | 10 | 23 |
| 18. | 14 | M | 6 | 0 | −4.3 | 1.5 | −5 | 3.9 | −4.5 | 1.3 | 125 | 145 | 28 | 26 |
| 19. | 18 | F | 6 | 0 | −6.3 | 4.2 | −5.8 | 4.3 | −4.3 | 1.4 | 130 | 140 | 8 | 20 |
| 20. | 68 | M | 5 | 0 | −5.7 | 4.8 | −7.5 | 5.3 | −6.5 | 1.2 | 110 | 145 | 5 | 23 |
| 21. | 18 | M | 4 | 0 | −3.9 | 2.5 | −5.4 | 4.3 | −4.5 | 1.1 | 100 | 158 | 12 | 25 |
| 22. | 17 | F | 4 | 1 | −5.3 | 2.5 | −4.8 | 3.9 | −4.3 | 1 | 130 | 156 | 3 | 24 |
| 23. | 17 | M | 5 | 1 | −11 | 2.3 | −12.5 | 2.1 | −10.2 | −1.2 | 90 | 158 | 2.4 | 27 |
| 24. | 37 | M | 4 | 0 | −14 | 2.4 | −16.4 | 3.4 | −10.1 | 1 | 83 | 148 | 13 | 28 |
| 25. | 23 | M | 5 | 0 | −14.3 | 2.1 | −17.3 | 2.9 | −9.3 | 1.4 | 94 | 148 | 14 | 29 |
| 26. | 30 | M | 5 | 1 | −11 | 2.7 | −13.5 | 3.2 | −11.4 | 1.6 | 92 | 147 | 3.4 | 26 |
| 27. | 38 | M | 5 | 0 | −13.8 | 3.5 | −15.3 | 3.9 | −12.3 | 1.8 | 120 | 154 | 3.6 | 26 |
| 28. | 16 | M | 5 | 0 | −12.9 | 3.6 | −15.4 | 3.8 | −11.2 | 1.4 | 110 | 156 | 3.2 | 27 |
| 29. | 23 | M | 4 | 1 | −14.2 | 3.7 | −16.3 | 2.1 | −13.2 | 1.2 | 110 | 153 | 3.4 | 28 |
| 30. | 38 | F | 5 | 0 | −12.9 | 4.3 | −15.3 | 1.3 | −10 | −1 | 140 | 156 | 4.5 | 29 |
| 31 | 21 | M | 5 | 0 | −18 | 3.6 | −15.3 | 1.2 | −6.7 | 1.2 | 130 | 154 | 4.6 | 29 |
| 32. | 48 | M | 6 | 1 | −19 | 3.8 | −16.6 | 2.9 | −18.3 | 1.5 | 124 | 156 | 3.2 | 24 |
| 33. | 15 | M | 7 | 0 | −19.4 | 3.6 | −20.3 | 2.8 | −12.7 | 1.5 | 142 | 158 | 3.5 | 24 |

TABLE 3-continued

Pre and post operative radiological findings

| Pt. no. | Age | Sex | Atlanto Dental Interval, ADI (mm) | | Chamberlain Line, CL (normal = 2.3 ± 2.6 mm) | | Mc Rae's Line, ML (normal = 5.8 ± 1.6 mm) | | Wackenheim Line, WL (normal = 0.9 ± 2.2 mm) | | Clivus Canal Angle, CCA(Normal > 150 deg) | | Modified Ranawat's Line, RL (Normal value: 29.7 ± 2.6 mm) | |
|---|---|---|---|---|---|---|---|---|---|---|---|---|---|---|
| | | | Pre op | Post op | Pre op | Post op | Pre op | Post op | Pre op | Post op | Pre op | Post op | Pre op | Post op |
| 34. | 12 | M | 7 | 0 | −17.5 | 3.2 | −14.2 | 2.4 | −11.2 | 1.6 | 124 | 142 | 2.3 | 23 |
| 35. | 32 | M | 6 | 1 | −13.9 | 2.1 | −11.3 | 2.8 | −10.5 | 1.7 | 126 | 158 | 1.5 | 18 |

Negative value indicates that the dens is placed above this line

Dynamic Distraction Couples with Cable Compression

In yet another embodiment of the invention, the instant application provides the surgical technique of dynamic distraction coupled with cable compression (DDCC) for intra-operatively correcting both Basilar Invagination (BI) and Atlanto-Axial Dislocation (AAD).

Figure 8:
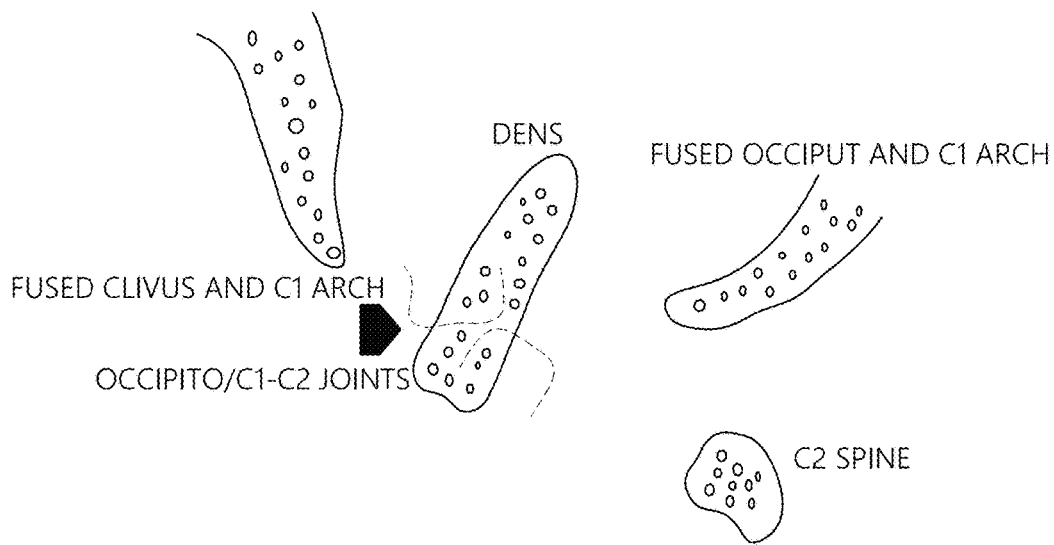
FIG. 8: The figure shows a schematic diagram in the sagittal section of a case of severe basilar invagination with fused C1 arch. It can be seen that the occipito/C1 and C2 joints are not apposed (arrow head, dotted lines) and there is a subluxation of C2 joint over C1 joint. In such an instance, DCER cannot be performed as the significant subluxation does not allow the placement of a spacer.

Though DCER is more effective than the earlier known surgical techniques to produce a movement in the horizontal direction, it does not allow the correction of posterior subluxation of the C2 joint in the saggital axis (FIG. 8). Dynamic distraction coupled with cable compression (DDCC) is a technique, which overcomes this shortcoming. By a combination of distraction, while compressing the posterior elements using a cable, it distracts and reduces the C1/C2 joint subluxation first. This allows for a proper placement of a spacer to allow an effective DCER to be performed.

Dynamic distraction coupled with cable compression (DDCC) may be especially utilized for the following indications:
1. Patients with saggital C2/C1 joint subluxation:
2. Patients with vertically oriented joints.

DDCC may be performed only in those cases where the C1 is occipitalized.

The procedure is performed under general anesthesia. The patient is positioned prone. A standard exposure posteriorly is performed and occiput, C1 arch and C2 arch will be exposed.

The technique consists of 3 steps:

Step I: The posterior margin of foramen magnum is drilled and joints on both the sides of the foramen magnum are exposed adequately.

Figure 9:
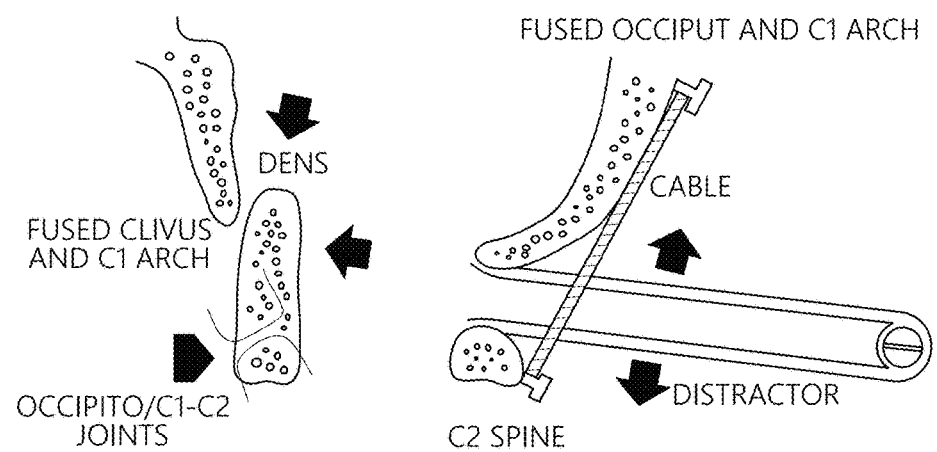
FIG. 9: The figure shows the fundamental concept of DDCC (Dynamic distraction coupled with cable compression). Following removal of the posterior rim of foramen magnum (Step I), 2 calipers are placed between the occiput and C2 pars bilaterally (Step II). A cable is then attached from C2 spinous process (may also be attached to C2 lamina by laminar hooks) to the occiput with help of screws. Now the calipers are gently distracted (arrows over calipers, Step III). Since the C2 spine and occiput is now held by a cable, and cannot be separated further, the basilar invagination and atlanto axial dislocation are both reduced by movement of the dens in a downward and forward direction.

Step II: Following this, 2 separate customized caliper distractors are positioned on either side of the foramen magnum. One arm of the distractor is placed under the occiput and the other arm over the C2 pars. The calipers are designed in such a manner, so that the arms of the calipers fit snugly under the occiput and over the C2 pars (FIG. 9).

Step III: A cable is then attached between the C2 spinous process and the occiput, using customized screws attached to both. The cable may be also attached to the C2 laminae by the aid of laminar clamps (FIG. 10). Both the calipers and the cable are generic devices, which are customized to be used for this technique. The calipers are then slowly distracted (FIG. 10). Since the separation of occiput and C2 spinous process is limited by the cable, basilar invagination now reduces with the dens moving forward and downward (FIG. 3). This also leads to reduction of the subluxed C1-C2 joints bringing them both in alignment with each other. A spacer now may be placed between them and DCER may be carried out as described earlier.

Since the cable restricts the separation of the posterior elements (occiput and C2 spine), the distraction now effectively reduces both the BI and AAD moving the dens in a downward and a forward direction. Hence this procedure has been named as dynamic distraction coupled with cable compression (DDCC).

The cable is also constructed in such a manner that it can be further shortened using calipers and a screw to tighten the cable (FIGS. 11A and B).

DDCC also provides the advantage of providing movement in two axis i.e. vertical and horizontal direction thus effectively reducing both BI and AAD. However unlike, DCER, there is no need to apply a spacer to provide motion in 2 axis. DDCC has the advantage to re-align the C2 and C1 joints in the saggital axis. Following correction, a standard DCER may be performed.

Surgical Instruments for Performing DCER and DDCC

The following presents a detailed description of various embodiments of surgical instruments with reference to the accompanying drawings.

The embodiments of the present subject matter are described in detail with reference to the accompanying drawings. However, the present subject matter is not limited to these embodiments which are only provided to explain more clearly the present subject matter to the ordinarily skilled in the art of the present disclosure. In the accompanying drawings, like reference numerals are used to indicate like components.

Both DCER and DDCC are highly complex procedure and the standard cervical spine instruments may not be convenient to use for the procedure adopted in the present subject matter; and require unique and customized set of instruments designed specially to carry out the intended procedure in the most efficient and effective manner.

However, the instruments as described in the present subject matter illustrates or suggests the general description based on the fundamental physiological principles and, the actual instruments intended to be used commercially are subjected to variations in size and dimensions etc. and are constructed based on the spinal bio-mechanical studies.

FIG. 11(A) represents the joint distractor (100) in accordance to an embodiment of the present subject matter. The joint distractor (100) can be designed and devised in different sizes so as to accommodate various age groups and different body masses. There is provided a set of two joint distractors in accordance to a preferred embodiment of the present subject matter; each for the right and left side joints that allows simultaneous bilateral distraction.

The joint distractor (100) as represented in FIG. 11(A) has an upper arm and a lower arm. The upper arm of the joint distractor (100) rests over the surface of the occiput (102) and has a flat surface or a foot plate provided with serrated margins (104) that helps allow a good grip over the occiput surface (102) as shown in FIG. 4(B). The lower arm is narrow and has a right angled curved hook that curves or rests over the C2 pars (114), going from lateral to medial part. The joint distractor (100) is right angled to provide an un-obstructed view i.e., to allow for adequate visualization of the joint spaces and, the distractors used in the present subject matter are self-retaining in nature.

Figure 12:
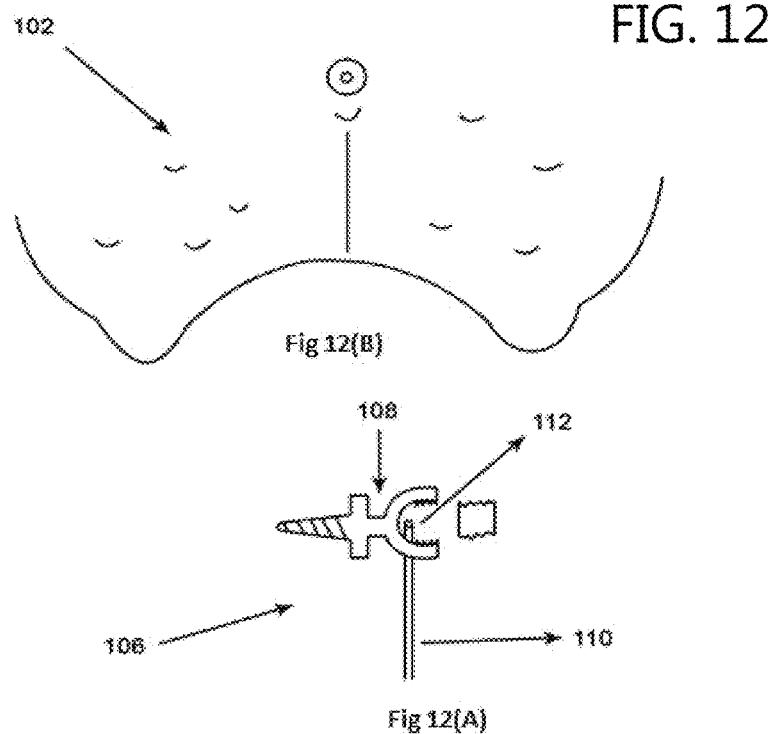
FIGS. 12(A) & 12(B): is a schematic representation of temporary occipital screw and its arrangement with the occiput respectively; and is in accordance with an embodiment of the present subject matter.

FIG. 12(A) represents a temporary occipital screw (106) used in accordance to an embodiment of the present subject matter. The temporary occipital screw (106) employed in the present subject matter is self-tapping in nature and can be designed and used in varying sizes as per the requirement and comfort.

The temporary occipital screw (106) as represented in FIG. 12(A) is used for holding an upper arm of the compressor and also for holding the cable (110) used in performing DDCC according to an embodiment of the present subject matter. The temporary occipital screw (106) has a slot (108) which holds the upper arm of the compressor used for both DCER and DDCC operations. The screw head (112) of the temporary occipital screw (106) places the cable (110) which is secured and held in place by tightening the inner screw.

Figure 13:
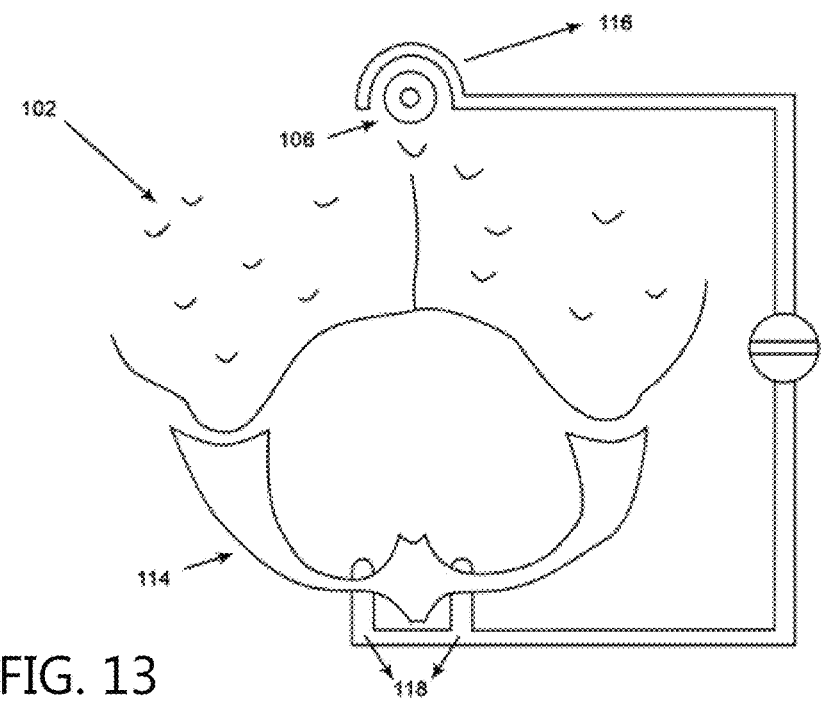
FIG. 13: is a schematic representation of the arrangement of cervico-occipital compressor with the occiput and, is in accordance with an embodiment of the present subject matter.

According to an embodiment of the present subject matter, there is also provided a cervico-occipital compressor as shown in FIG. 13 The cervico-occipital compressor is used for performing compression required in both DCER and DDCC. It helps perform the compression component of DCER and also the cable compression required for DDCC i.e., to compress the cable (110) while there is gradual tightening of the cable (110) between the occiput (102) and C2 (114).

The cervico-occipital compressor as used in the present subject matter is provided with two arms and, the upper arm of the cervico-occipital compressor has a semi circle hook (116) which fits on the slot (108) of the temporary screw (106) over the occiput (102) as shown in FIGS. 12(A) & (B). The lower arm of the cervico-occipital compressor has two laminar hooks or clamps (118) which pass under the laminae on either sides of the C2 spine as shown in FIG. 13.

FIG. 14(A) represents a double headed screw used for C2 pars (114) in accordance to an embodiment of the present subject matter. The screw head (124) of the double headed screw as used in the present subject matter is poly axial and accommodates two rods placed in two different directions. The double headed screw is employed for convenient placement of two rods i.e., holding or placing one rod (120) from the midline occiput (102) to C2 pars (114) and another rod (122) from C2 pars (114) to C3-C6 lateral masses. There is a requirement of using the double headed screw as it is difficult to contour the same rod for cervico-occipital fixation i.e., the angulation of rod placement from midline occiput till C2 pars is different from C2 pars to lateral masses of C3-C6.

It is in accordance to an embodiment of the present subject matter that there is provided a connector (126) connecting the C2-occiput rod and C3 lateral mass screw as shown in FIG. 15. The connector (126) appears like a longer offset with sizes varying from 20 mm till 50 mm and subjected to variations as per the requirement. The connector (126) as incorporated in the present subject matter serves an important function of strengthening the C2-occipital connection by connecting it to C3 lateral mass screw.

It is to be understood that the above described embodiments are merely illustrative principles of the present subject matter and that many variations may be devised by those skilled in the art without departing from the scope of the present subject matter. It is, therefore, intended that such variations be included with the scope of the claims.

REFERENCES

1. Ahmed R, Traynelis V C, Menezes A H. Fusions at the craniovertebral junction. Childs Nery Syst 2008; 24:1209-1224.
2. Goel A, Desai K, Bhatjiwale M, Muzumdar D P. Basilar invagination and Chiari malformation associated with cerebellar atrophy: report of two treated cases. Journal of clinical neuroscience: official journal of the Neurosurgical Society of Australasia 2002; 9:194-196.
3. Dickman C A, Locantro J, Fessler R G. The influence of transoral odontoid resection on stability of the craniovertebral junction. Journal of neurosurgery 1992; 77:525-530.
4. Goel A, Sharma P. Craniovertebral junction realignment for the treatment of basilar invagination with syringomyelia: preliminary report of 12 cases. Neurologia medico-chirurgica 2005; 45:512-517; discussion 518.
5. Goel A, Sharma P. Craniovertebral realignment for basilar invagination and atlantoaxial dislocation secondary to rheumatoid arthritis. Neurology India 2004; 52:338-341.
6. Wang X W, Jian F Z, Chen Z, Wu H, Bao Y H. [An analysis of surgical outcome and influencing factors in patients of congenital basilar invagination with atlantal-axial dislocation: report of 120 cases]. Zhonghua Wai Ke Za Zhi 2013; 51:207-210.
7. Wang Y, Wang L, Zhang W, Zhang P, Tan H, Liu Y. [Assembling and clinical application of video output system utilizing teaching sight glass of surgical microscope]. Zhongguo Xiu Fu Chong Jian Wai Ke Za Zhi 2011; 25:323-326.
8. Jian F Z, Chen Z, Wrede K H, Samii M, Ling F. Direct posterior reduction and fixation for the treatment of basilar invagination with atlantoaxial dislocation. Neurosurgery 2010; 66:678-687; discussion 687.
9. Hsu W, Zaidi H A, Suk I, Gokaslan Z L, Wolinsky J P. A new technique for intraoperative reduction of occipitocervical instability. Neurosurgery 2010; 66:319-323; discussion 323-314.
10. Chandra P S. In reply. Neurosurgery 2014; 74:E148-150.

I claim:

1. A method to reduce basilar invagination (BI) and atlanto-axial dislocation (AAD) comprising:
    applying a single stage posterior approach to a patient undergoing neurosurgery, wherein said single stage posterior approach comprises distraction, compression, and extension reduction over a fulcrum provided by a joint spacer and, wherein said method further comprises:
    a. removal of posterior margin of the foramen magnum;
    b. distraction and placement of a spacer leading to vertical reduction of basilar invagination; and
    c. compression and extension of C1 or occipitilized C1 over C2 utilizing the fulcrum created by placement of the spacer leading to reduction of atlanto-axial dislocation.

2. The method according to claim 1, wherein, the removal of the posterior margin of the foramen magnum is performed by drilling.

3. The method according to claim 1, wherein the distraction is facilitated by placing the arms of the distractor between the occiput superiorly and the upper body of the C2 inferiorly.

4. The method according to claim 1, wherein, the spacers are placed bilaterally within the joint space on both sides of the foramen magnum.

5. The method according to claim 1, wherein said patient has a C1 arch that is not assimilated.

6. The method according to claim 5, wherein C1 lateral mass screws and C2 trans-laminar screws are placed followed by placing of an offset connected to a laminar clamp over the C1 arch.

7. The method according to claim 5, wherein compression is performed with the tips of blades placed superiorly between the offset and the laminar clamp and inferiorly below the C2 screw.

8. The method according to claim 1, wherein the C2 trans-laminar screws are placed followed by placement of a temporary occipital screw, which is then attached to an offset that acts as one of the holding points for the compressor.

9. The method according to claim 1, wherein compression is performed by placing one arm of the compressor over the offset, attached to the temporary occipital screw, superiorly and under the trans-laminar screws inferiorly.

10. The method according to claim 1, wherein a rod is fixed to the trans-laminar screw below and to the occipital screw above.

11. The method according to claim 1, wherein said patient has a C1 arch that is assimilated with the occiput.

12. A method to reduce basilar invagination (BI) and atlanto-axial dislocation (AAD) comprising:
applying a single stage posterior approach to a patient undergoing neurosurgery, wherein said single stage posterior approach comprises dynamic distraction cable compression, and extension reduction and, wherein said method further comprises:
  a. drilling the posterior margin of foramen magnum till joints on either side are exposed;
  b. positioning two separate customized caliper distracters on either side of the foramen magnum;
  c. attaching a cable between the C2 spinous process and the occipit or to the C2 laminae;
  d. distraction of calipers; and
  e. placement of a spacer.

13. The method as claimed in claim 12, wherein the caliper distracters are positioned by placing one arm of the distractor under the occiput and the other arm over the C2 pars.

14. The method as claimed in claim 12, wherein, the cable is attached between the C2 spinous process and the occipit using screws attached to both.

15. The method according to claim 12, wherein, the spacer is placed bilaterally within the joint space on both sides of the foramen magnum.

16. The method according to claim 12, wherein, distraction, compression and extension reduction is performed following placement of the spacer.

17. A system for performing distraction, compression, and extension reduction (DCER) and dynamic distraction coupled with cable compression (DDCC) comprising:
at least one self-retaining joint distractor having an upper arm and a lower arm;
a self-tapping temporary occipital screw for holding an upper arm of a compressor and a cable;
a cervico-occipital compressor having an upper arm and a lower arm;
a double headed screw for placing rods from the occiput to C2 pars and from said C2 pars to C3-C6 lateral masses; and
a connector connecting said C2-occiput rod to C3 lateral mass screw.

18. The system as claimed in claim 17, wherein there are two sets of said joint distractor for right and left side joints respectively.

19. The system as claimed in claim 17, wherein said upper arm of said joint distractor has a flat surface with serrated margins for gripping the occiput surface.

20. The system as claimed in claim 17, wherein said lower arm of said joint distractor is right angled to rest over said C2 pars.

21. The system as claimed in claim 17, wherein said temporary occipital screw has a slot for holding said upper arm of said compressor.

22. The system as claimed in claim 17, wherein said temporary occipital screw has a screw head for placing said cable thereof and an inner screw for holding said cable.

23. The system as claimed in claim 17, wherein said upper arm of said cervico-occipital compressor is a semi-circular hook and fits over the slot of said temporary occipital screw.

24. The system as claimed in claim 17, wherein said lower arm of said cervico-occipital compressor comprises two laminar hooks passing under C2 laminae on either sides of C2 spine.

25. The system as claimed in claim 17, wherein said double headed screw is a polyaxial screw.

* * * * *